(12) United States Patent
Liu et al.

(10) Patent No.: US 7,618,826 B2
(45) Date of Patent: Nov. 17, 2009

(54) MEMBRANE SUPPRESSOR WITH AN OUTLET SUBSTANTIALLY NON-RETENTIVE FOR IONIC SPECIES

(75) Inventors: Yan Liu, Palo Alto, CA (US); Victor Barreto, Campbell, CA (US); Christopher A. Pohl, Union City, CA (US)

(73) Assignee: Dionex Corporation, Sunnyvale, CA (US)

( * ) Notice: Subject to any disclaimer, the term of this patent is extended or adjusted under 35 U.S.C. 154(b) by 466 days.

(21) Appl. No.: 11/524,513

(22) Filed: Sep. 19, 2006

(65) Prior Publication Data

US 2008/0069731 A1    Mar. 20, 2008

(51) Int. Cl.
*G01N 30/02* (2006.01)
*G01N 33/00* (2006.01)

(52) U.S. Cl. .................. 436/161; 73/61.41; 210/198.2; 422/70

(58) Field of Classification Search ............... 210/198.2; 436/161
See application file for complete search history.

(56) References Cited

U.S. PATENT DOCUMENTS

| | | | |
|---|---|---|---|
| 3,897,213 A | 7/1975 | Stevens et al. | |
| 3,920,397 A | 11/1975 | Small et al. | |
| 3,925,019 A | 12/1975 | Small et al. | |
| 3,926,559 A | 12/1975 | Stevens | |
| 5,045,204 A | 9/1991 | Dasgupta et al. | |
| 5,248,426 A | 9/1993 | Stillian et al. | |
| 6,027,643 A | 2/2000 | Small et al. | |
| 6,325,976 B1 | 12/2001 | Small et al. | |
| 6,328,885 B1 | 12/2001 | Srinivasan et al. | |
| 6,468,804 B1 | 10/2002 | Anderson, Jr. et al. | |
| 6,495,371 B2 | 12/2002 | Small et al. | |
| 6,508,985 B2 | 1/2003 | Small et al. | |
| 6,562,628 B1 | 5/2003 | Liu et al. | |
| 6,610,546 B1 | 8/2003 | Liu et al. | |
| 6,682,701 B1 | 1/2004 | Liu et al. | |
| 2004/0149581 A1 | 8/2004 | Srinivasan et al. | |
| 2006/0057733 A1 | 3/2006 | Liu et al. | |

FOREIGN PATENT DOCUMENTS

WO    WO2004/024302 A1    3/2004

*Primary Examiner*—Jill Warden
*Assistant Examiner*—Timothy G Kingan
(74) *Attorney, Agent, or Firm*—Morgan, Lewis & Bockius LLP; David J. Brezner

(57) ABSTRACT

An apparatus for ion chromatography comprising a suppressor comprising a housing and a liquid conduit segment disposed in the housing, the liquid conduit segment including a membrane, the membrane having an inlet section adjacent the inlet of the conduit segment and an outlet section adjacent the outlet of the conduit segment, the inlet section having ion exchange sites capable of transmitting ions of one charge, positive or negative, and the outlet section being substantially non-retentive electrostatically for charged ionic species. Also, the method of using the apparatus.

22 Claims, 10 Drawing Sheets

MEMBRANE SUPPRESSOR WITH AN OUTLET SUBSTANTIALLY NON-RETENTIVE FOR IONIC SPECIES

BACKGROUND OF THE INVENTION

Ion chromatography has become a widely used analytical technique for the determination of anionic and cationic analytes in various sample matrices since it was introduced in 1975. Even though ion chromatography today comprises a number of separation and detection modes, ion chromatography with suppressed conductivity detection remains the most widely practiced form of the technique. In suppressed conductivity detection, an eluent suppression device, or suppressor, is the critical system component used to suppress the eluent, i.e., convert the eluent into a weakly conducting form and enhance the conductance of target analytes. The original suppressors were simply columns packed with ion-exchange resins in appropriate ionic forms. Those packed-bed suppressors required frequent off-line chemical regeneration. To overcome this problem, suppressors based on ion-exchange fibers and membranes were developed. These suppressors can be continuously regenerated using either acid or base regenerant solutions.

One electrolytically-regenerated membrane suppressor is disclosed in U.S. Pat. No. 6,328,885 (the '885 patent). In this device, the suppressor includes at least one regenerant compartment and one chromatographic effluent compartment separated by an ion exchange membrane sheet. The sheet allows transmembrane passage of ions of the same charge as its exchangeable ions. Spaced electrodes are disclosed in communication with both regenerant chambers along the length of the suppressor. By applying an electrical potential across the electrodes, there is an increase in the suppression capacity of the device. U.S. Pat. No. 5,248,426 describes a suppressor of the general type described in the '885 patent in an ion chromatography system in which the effluent from the detector is recycled to the flow channel(s) in the suppressor adjacent the sample stream flow channel.

U.S. Pat. No. 6,328,885 describes methods and apparatus for increasing the current efficiency of suppressor and suppressor-like pretreatment devices similar to those described in U.S. Pat. No. 5,248,426. In one embodiment, an aqueous sample stream including analyte ions of one charge and matrix ions of opposite charge flows through a sample stream flow channel, while flowing an aqueous stream through an ion receiving flow channel separated therefrom by a first ion exchange membrane, and passing a current between the channels to reduce the concentration of the matrix ions. The sample stream flow channel has an upstream sample stream portion containing the matrix ions and an adjacent downstream portion in which the matrix ions have been suppressed. The upstream portion has an electrical resistance no greater than about 0.9 times that of the downstream portion. The ion receiving flow channel includes stationary flow-through first packing of ion exchange material. Neutral or low capacity packing may be disposed in the sample stream flow channel.

U.S. Pat. Nos. 6,325,976, 6,495,371, 6,508,985, 6,562,628, and 6,610,546 describe continuous electrolytically regenerated packed bed suppressors for ion chromatography.

U.S. Patent Application "Capillary Ion Chromatography," Publication No. 2006/0057733, published Mar. 16, 2006 (herein, the '733 Publication), also describes several different electrolytic suppressors. In one embodiment, the suppressor includes a cation exchange capillary tubing embedded inside a bed of cation exchange resin housed in plastic column housing with flow-through ports. The inlet of the resin bed is fitted with a flow-through anode and the outlet of the resin bed is fitted with a flow-through cathode. Both electrodes are disclosed in direct contact with the resin packing. In the operation of this type of electrolytic capillary suppressor, the resin bed is continuously regenerated by hydronium ions generated through the electrolysis of water at the device anode.

The electrolytically-regenerated suppressors developed so far offer several advantages in ion chromatography. They provide continuous and simultaneous suppression of eluents, regeneration of the suppression bed, and sufficient suppression capacity for all common IC applications. They are easy to operate because the suppressed eluent or water is used to create regenerant ions electrolytically and there is no need to prepare regenerant solutions off-line. They are compatible with gradient separations. They have very low suppression zone volume, which makes it possible to achieve separations with very high chromatographic efficiency.

During the operation of ion chromatographic system, it is possible that the suppressor chromatographic effluent channel becomes exhausted if the electrical current is inadvertently turned off due to operator errors or instrument malfunctions. It is also possible that the suppressor chromatographic effluent channel become exhausted because the applied current to the suppressor is too low relative to the concentration of chromatographic eluent. The specific purpose of the suppressor stage in ion chromatography is to reduce the conductivity and noise of the analysis stream background while enhancing the conductivity of the analytes (i.e., increasing the signal/noise ratio) and maintaining chromatographic efficiency. When the suppressor chromatographic effluent channel becomes exhausted, the ion exchange sites are converted to the form of eluent cations (e.g., sodium form if a suppressor is used to suppress sodium hydroxide), analyte ions (e.g., chloride ions) exit the suppressor in the less conductive salt form (i.e., NaCl) instead of the more conductive acid form (i.e., HCl), and the conductivity of the analytes may becomes significantly smaller, which has obviously detrimental effects in analytical determination of the target analytes using ion chromatography. It is thus highly desirable that an exhausted electrolytic suppressor recovers rapidly upon application of appropriate amount of electrical current.

However, the prior-art electrolytic suppressors discussed above may not be fully regenerated rapidly upon application of electric field in the event that the chromatographic effluent channels become exhausted. In the prior-art electrolytic suppressors, the bulk of the chromatographic effluent channel is located within the electromigration pathway of regenerant ions and can be electrolytically regenerated rapidly. However, some ion exchange sites associated with outlet regions of the chromatographic effluent channels of the prior-art electrolytic suppressors may be located outside of the electromigration pathway of regenerant ions, and those ion exchange sites may not be electrolytically regenerated. In an electrolytic suppressor used for the determination of the target analyte anion ($X^-$), the ion exchange sites in the outlet region of the suppressor chromatographic effluent channel would remain in the form of eluent cations (e.g., sodium form if it is used to suppress sodium hydroxide) even after the bulk of ion exchange sites associated with the chromatographic effluent channel are electrolytically regenerated into the hydronium form. The target analyte ions (X−) are first converted to the desired and more conductive form ($H^+X^-$) for conductivity detection as they travel thorough the bulk of the chromatographic effluent channel. As the analyte ions travel further past the ion exchange sites in the outlet region of the suppressor chromatographic effluent channel, some target analyte ions are converted into the undesired and less conductive form ($Na^+X^-$). The presence of target analyte ions in two forms ($H^+X^-$ and $Na^+X^-$) in varying ratio leads the varying conductivity response of the target analyte ions and is detrimental to accurate determination of the target analyte. This behavior of the electrolytic suppressor remains until all ion exchange sites originally in the sodium form are converted into the hydronium form, which can be a slow process depending on the design of the electrolytic suppressor. Thus, the slow recovery of electrolytic suppressor can hamper its performance in ion chromatography.

SUMMARY OF THE INVENTION

One embodiment of the present invention is an apparatus for ion chromatography comprising a suppressor comprising a housing and a liquid conduit segment disposed in the housing, the liquid conduit segment including a membrane, the membrane having an inlet section adjacent the inlet of the conduit segment and an outlet section adjacent the outlet of the conduit segment, the inlet section having ion exchange sites capable of transmitting ions of one charge, positive or negative, and the outlet section being substantially non-retentive electrostatically for charged ionic species.

Another embodiment is an ion chromatography method comprising flowing an aqueous stream comprising separated ionic species of one charge, positive or negative, in an eluent through a suppressor comprising a liquid conduit segment including a membrane, said membrane having an inlet section adjacent the inlet of said conduit segment and an outlet section adjacent the outlet of said conduit segment, said inlet section having ion exchange sites capable of transmitting ions of one charge, positive or negative, said outlet section being substantially non-retentive electrostatically for charged ionic species, to transport counter ions in said eluent of opposite charge to said separated ionic species out of said conduit segment across said membrane.

DETAILED DESCRIPTION OF THE PREFERRED INVENTION

Figure 1:
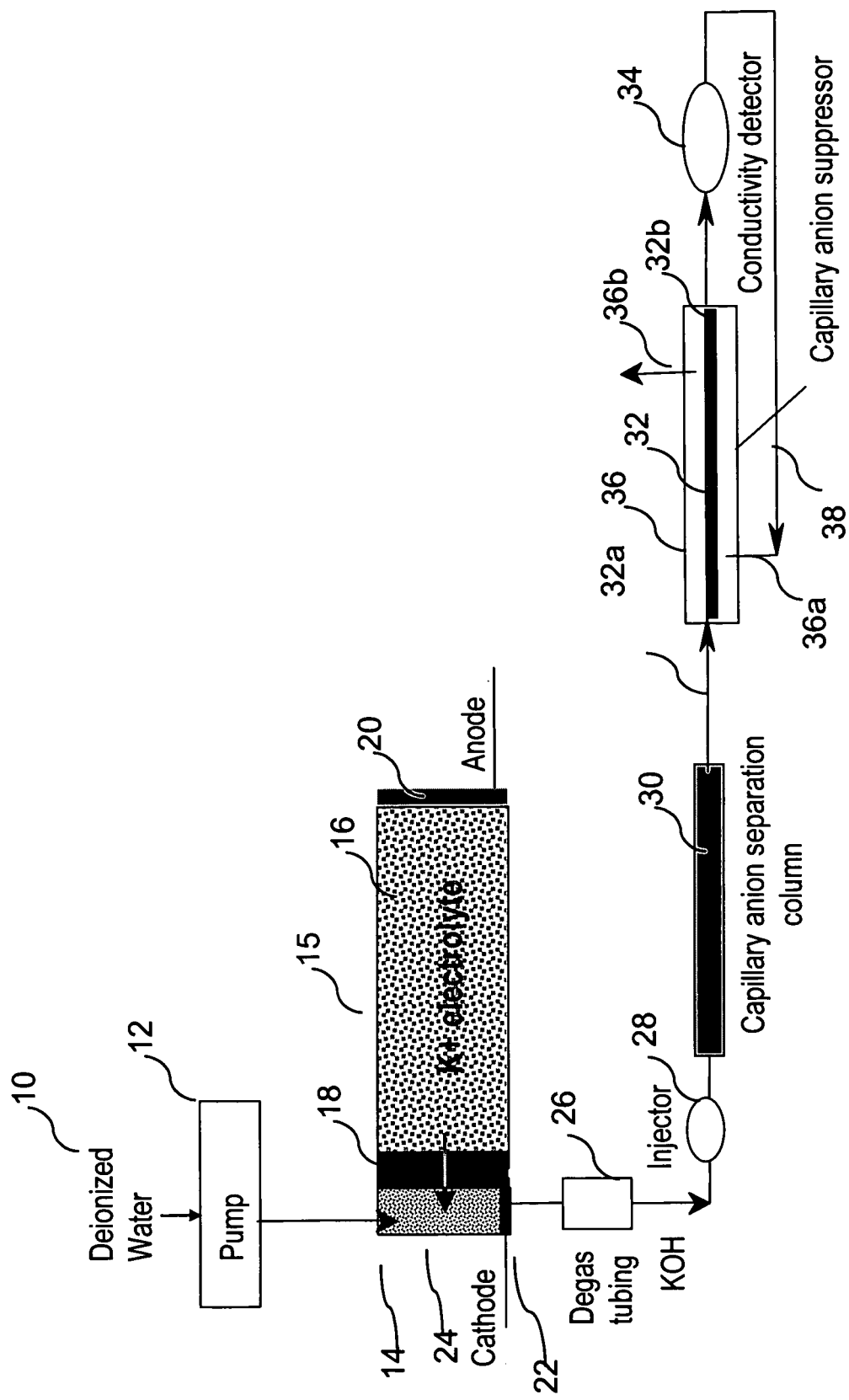
FIGS. 1-5 are schematic representations of different embodiments of the present invention.

The system of the present invention is useful for determining a large number of ionic species. The species to be determined are solely anions or solely cations. Suitable samples include surface waters, and other liquids such as industrial chemical waste, body fluids, beverages, and drinking water. When the term "ionic species" is used, it includes species in ionic form and components of molecules which are ionized under the conditions of the present invention.

The present invention relates to a membrane suppressor device which can be a planar membrane suppressor, e.g., of the type illustrated as an electrolytic membrane suppressor described in the '885 patent. Alternatively, the membrane suppressor in tubular form such as described in the '733 Publication for a capillary suppressor. The common element for the suppressors of the present invention is that they include a housing a liquid conduit segment disposed in the housing. The conduit includes an ion exchange membrane with an inlet section adjacent the inlet of the conduit segment and an outlet section adjacent the outlet conduit segment. The inlet segment has ion exchange sites capable of transmitting ions of one charge, positive or negative.

The outlet section is substantially non-retentive electrostatically for charged ionic species, also referred to herein as "substantially non-retentive." This means that no substantial amount of charged ionic species in a sample would be retained by the outlet section. In one embodiment, the outlet section is substantially free of ion exchange sites, also termed "non-functionalized," "unfunctionalized," or "neutral." Typically, in this embodiment, such outlet section has less than 5% to as low as 0% of the ion exchange capacity of a fully functionalized outlet section.

In another embodiment, the substantially non-retentive electrostatically outlet section has functionally balanced ion exchange sites of positive and negative charges (e.g., such opposite charges are of substantially the same intensity and closely proximate to each other so no substantial amount of ionic species are retained electrostatically compared to an outlet section of positive or negative charge).

This application will be described with respect to an outlet section which is substantially free of ion exchange sites, first describing a suppressor used in ion chromatography for a capillary system. Then it will describe it in the form of a membrane sheet suppressor such as described in the '885 patent. The description of the membrane with the charged inlet and uncharged outlet will follow the descriptions of general systems in which it can be used.

In one embodiment, the present invention relates to ion chromatography apparatus and method in which the chromatography is performed on a capillary scale. Ion chromatography systems of the present invention include (a) a capillary separation column, typically in the form of a chromatography column, (b) a suppressor in which the effluent from the chromatography column flows through a capillary-sized tubing in the suppressor ("a capillary suppressor"), and (c) a detector, typically a conductivity detector, downstream of the suppressor The term "capillary tubing" is defined to encompass narrow bore capillary tubing as generally used in chemical analysis but is not limited to such capillary tubing. Instead, the term "capillary tubing" broadly includes tubing having the dimensions on the order of magnitude of the internal dimensions of prior art capillary tubing. Such capillaries typically have a bore diameter ranging from about 5 to 1,000 microns, more preferably from about 10 to 500 microns. Such dimensions typically apply both to the separator column and the suppressor capillary tubing of the present invention. One or more segments of capillary tubes may be joined to form continuous capillary tubing. The capillary tubing is typically used under the conditions of capillary flow rates, e.g. 0.1 to 50 μL/min.

The invention also is application to non-capillary conduits that include a segmented membrane with an ion exchange inlet section and a non-functionalized outlet suitable for ion chromatography.

In general, the invention is applicable to any of the well-known ion chromatography systems such as those illustrated in U.S. Pat. Nos. 3,897,213, 3,920,397, 3,925,019 and 3,926,559. These patents and the other patents and Publications referred to herein are incorporated by reference.

In one embodiment of the invention, illustrated in FIG. 1 herein and in the '733 Publication, the suppressor of the present invention is illustrated schematically in the form of a capillary suppressor. In this embodiment, an eluent generator of the type illustrated in FIG. 1 of U.S. Pat. No. 6,682,701 is used, although other eluent generators as illustrated in that patent or elsewhere can be used in combination with the capillary ion chromatography system of the present invention. The principles of operation of the eluent generator are fully illustrated in this patent. Also, the system of FIG. 1 illustrates a recycle of solution from the detector to the outside of the capillary tubing. Such recycle for different forms of suppressors is illustrated in U.S. Pat. No. 5,248,426.

Referring specifically to the embodiment of FIG. 1, deionized water from a source, not shown, is pumped by pump 12 through high pressure base generator chamber 14 of base generator 15. Chamber 14 is separated from a low pressure ion source reservoir 16 including a source of eluent ion. As illustrated, the system is for anion analysis in which the ions to be supplied for the analyte are cations, potassium ion as illustrated, or sodium, lithium or other cations. The ion source reservoir 16 may be in the form of a base or salt solution which can be replenished as illustrated in the '701 patent. A charged permselective membrane barrier or connector 18 substantially prevents bulk liquid flow while providing an ion transport bridge to transport the potassium ions into the base generation chamber 14. Suitable membranes, e.g. ones formed of Nafion®, for use as the inlet section of the membrane, are described in the '701 patent. An anode 20, e.g. platinum, is in electrical communication with reservoir 16 and a cathode 22, e.g. platinum, is disposed at the outlet of base generation chamber 14. Cation exchange packing such as a resin bed may be disposed in base generation chamber 12 as illustrated in the '701 patent. Electrolysis is performed to provide the reaction illustrated in the '701 patent so that the base, KOH, is generated in base generation chamber 14. Under the applied electric field, the potassium ions migrate across the ion exchange connector or membrane to combine with hydroxide ions to form a KOH eluent. The concentration of KOH solution formed is proportional to the applied current and inversely proportional to the flow rate of the deionized water carrier stream. Hydrogen is generated at the cathode which could interfere with analysis. Thus, it is preferable to use a degassing tubing device 26 typically using a porous membrane to remove generated hydrogen gases, also illustrated in the '701 patent.

Sample is injected in injector 28 and is carried by the eluent from base generator 15 to ion exchange chromatographic separation column 30. For anion analysis, separation is performed using anion separation medium, typically a packed bed of ion exchange resin in column 30, but of a capillary dimension, as set forth above.

As illustrated, the effluent from capillary anion separation column 30 flows to the inlet 32a of capillary tubing 32, then through the tubing and out outlet 32b and through detector 34, suitably a conductivity detector. Tubing 32 is contained within a suppressor housing 36 which can be any shape including tubular or rectangular. The effluent from the detector 34 is recycled in line 38 to an inlet port 36a of housing 36 and flows outside tubing 32 preferably countercurrently to the flow in tubing 32, and exits outlet port 36b.

Capillary tubing 32 is formed of a permselective ion exchange membrane, suitably of the type described in the prior art, such as formed of Nafion®, to block bulk liquid flow but permit transport of the selected ion, cation in the instance of anion analysis. Thus, the wall of the tubing serves the same purposes as a prior art membrane suppressor or a membrane barrier 18 which can also be formed of Nafion®. The details of the suppressor will be described below. While the system of the tubular embodiment of the invention is described in the context of a capillary system, the invention is also applicable to conduits of a larger internal diameter. These conduits may be packed with appropriate ion exchange materials in manners similar to those disclosed in U.S. Pat. No. 5,248,426.

Other eluent generators may be used with an ionized water source, such as a generator for a carbonate salt such as potassium carbonate illustrated in PCT Application WO/2004/024302. In this instance, the ion chromatography system downstream from the eluent generator also is as illustrated in FIG. 1. Other eluent generators which can be used are illustrated in U.S. Pat. No. 5,045,204 or U.S. Pat. No. 6,562,628.

Although the eluent generators are illustrated for anion analysis and the generation of cations such as potassium ions, for cation analysis, the same system may be used for generating MSA or other anions for an eluent by appropriate reversal of the polarity of the membrane ion exchange resin and electrodes such as illustrated in U.S. Pat. No. 6,682,701.

It is apparent that the system of FIG. 1 including eluent generation as illustrated above is capable of performing the entire ion chromatography separation process including analyte separation, eluent suppression, and analyte detection using one or more flowing streams of deionized water.

Figure 2:
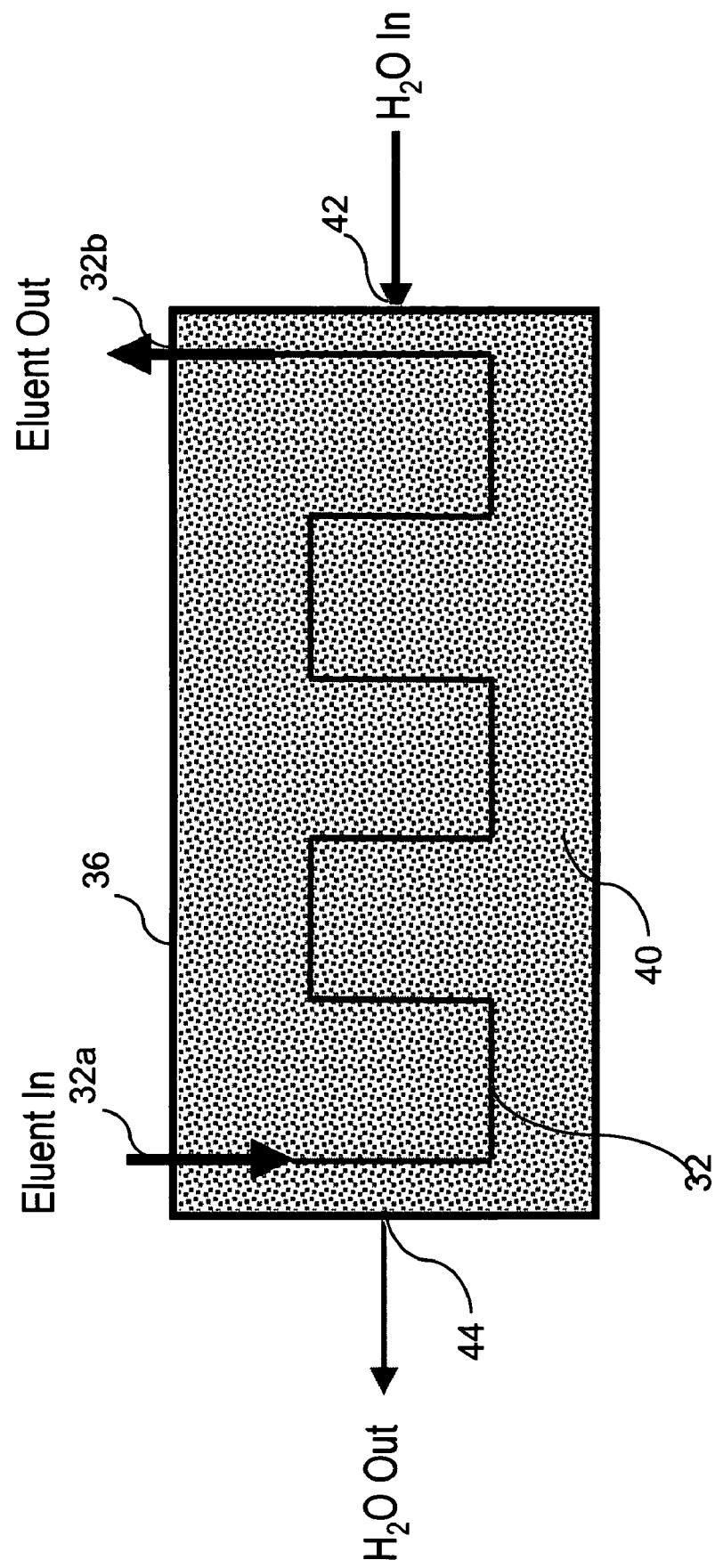

FIG. 2 schematically illustrates an embodiment of a capillary suppressor according to the present invention. Like parts will be designated below with like numbers for FIGS. 1 and 2. As illustrated, suppressor housing 36, suitably formed of a non-conductive, e.g. plastic, column with flow-through ports, include capillary tubing 32 with an inlet 32a and outlet 32b. The tubing typically projects through liquid tight fittings into and out of housing 36 and project in direct or indirect fluid communication with the outlet of separation column 30. Outlet 32b of tubing 32 projects through the housing and is connected to tubing for fluid communication with the inlet of flow-through detector 34.

For anion analysis, the capillary tubing is preferably tightly embedded in cation exchange packing 40, suitably a cation exchange resin bed in direct contact therewith. Packing 40 is contained in a housing 36. As illustrated, separate fluid connections are used for the stream flowing through the capillary tubing. A source of flowing aqueous regenerant liquid flows through packing 40 from inlet 42 in a conduit and through outlet 44 through appropriate fittings. In the embodiment of FIG. 1, the water source for inlet 42 is the sample stream effluent from the conductivity detector after detection as illustrated in FIG. 1 which flows in recycle conduit 38 illustrated in FIG. 1.

In one embodiment of the suppressor for anion analysis described in the '733 Publication, the inlet section of capillary tubing 32 is made of a Nafion® membrane material or some other form of strongly acidic cation exchange membrane. A typical length of the capillary tubing within the suppressor is about 0.1 to 50 cm, preferably 1 to 20 cm. Preferable internal diameters are between about 0.001 inch to 0.010 inch. In one embodiment, the cation exchange resin for ion separation is preferably a strongly acidic cation exchange resin such as sulfonated resin in the hydronium ion ($H^+$) form.

As used herein, the terms "strongly acidic cation" exchange resin or functional groups as those terms are used in the field of chromatography. Thus, for example, Dowex 50W X8 and Amberlite IR 122 are commonly used strongly acidic cation exchange resins. In this type of resin, the functional groups are typically strong acids with pKa less than 1. Typical strongly acidic functional groups include sulfonic groups.

As used herein, the terms "weakly acidic cation" exchange resin or functional groups as those terms are used in the field of chromatography. Thus, for example, Chelex-100 and Bio-Rex 70, and Amberlite IRC-76 resins are commonly used weakly acidic cation exchange resins. In this type of resin, the functional groups are typically weak acids with pKa greater than 1. Typical weakly acidic functional groups include carboxylic acid, chlorocarboxylic acid, and phosphonic acid groups.

Well-known cation exchange packing 40 in the hydronium form may also be used in this embodiment. Although packing 40 is described in a preferred form of ion exchange resin bed, other forms of packing may be used such as a porous continuous structure with sufficient porosity to permit flow of solution through without undue pressure drop and with sufficient ion exchange capacity to form a conducting bridge of cations or anions between the electrodes. One form of structure is a porous matrix or a sponge-like material formed of sulfonated, cross-linked polystyrene with a porosity of about 10 to 90% permitting a flow rate of about 0.01 to 20 ml/min. without excessive pressure drop.

In an embodiment not shown, if the flow rate of the sample liquid stream in recycle conduit 38 is insufficient for its desired effects carrying away the ions which transport across the wall of tubing 32 and/or for cooling the suppressor for an electrolytic application, then an additional source of flowing aqueous liquid, not shown, may be directed through packing 40. In this instance, the additional source of aqueous liquid may comprise a water stream, e.g. deionized water, which is pumped to the suppressor and either combines into a single stream with the water in the recycle conduit or can be directed in a separate conduit through packing 40. As with suppressors which include the recycle in the prior art, it is preferable to flow the aqueous water through the packing external to the tubing countercurrently to flow in the tubing.

When the aqueous effluent from the conductivity detector is recycled and routed through packing 40, the suppressor can be continuously regenerated as long as there is a continuous flow of water to remove KOH generated in the hydrolysis of the weakly acidic resin in the potassium form. Depending on the chemical properties of the functional groups on the resin, the kinetics of the hydrolysis may become a limiting factor determining the suppression capacity of device with respect to the influx of KOH eluent into the suppressor. A second stream of deionized water flowing through the resin bed of the suppressor which may be at a flow rate higher than the flow rate used in the separation process is preferred since it is expected that the suppression capacity may be improved.

For anion analysis as described in the '733 Publication, capillary tubing with a sulfonated membrane is used, as a base eluent (e.g., KOH) enters the capillary tubing, potassium ions (K$^+$) exchange with hydronium ions (H$^+$) in the wall of the capillary according to the following equations:

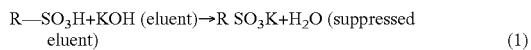

$$R\text{—}SO_3H + KOH \text{ (eluent)} \rightarrow R\,SO_3K + H_2O \text{ (suppressed eluent)} \tag{1}$$

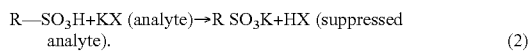

$$R\text{—}SO_3H + KX \text{ (analyte)} \rightarrow R\,SO_3K + HX \text{ (suppressed analyte)}. \tag{2}$$

In the equation, R represents an ion-exchange surface on the capillary inlet section. Since the cation exchange capillary is in direct physical contact with the bed of cation exchange resin, K+ ions originally exchanged onto the wall of the cation exchange capillary continue to exchange with H+ ions on the resin beads immediately adjacent to the wall. Subsequently, this exchange process continues to occur among the resin beads that are not in direct physical contact with the cation exchange capillary and located further way from the capillary tubing. In this process, cation exchange resin beads become the source of regenerant ions (i.e., H+ ions) to regenerate the cation exchange capillary tubing. The suppression process continues until the point when the cation exchange beads surrounding the cation exchange capillary become predominantly in the potassium form and the incoming flux of hydronium ions to the cation exchange capillary drop to a level that is insufficient to neutralize the incoming KOH eluent.

The effective suppression capacity of the device at a given eluent concentration and flow rate depends on a number of factors including the length of the capillary, the eluent flow profile inside the capillary, the resin ion exchange capacity, the resin particle size, the amount of the resin surrounding the capillary, the resin bed geometry and the like. The capillary tubing can be woven into a geometrical pattern to create torturous flow paths for the eluent going through the capillary to increase the contact of the eluent with the wall of the capillary in order to increase the suppression capacity of the device. The internal opening of the inlet section of the capillary may also be filled with an inert or cation exchange monofilament to decrease the dead volume of the capillary suppressor as well as to increase the contact of the eluent with the wall of the capillary in order to increase the suppression capacity of the device. Once the effective suppression capacity of the suppressor is consumed, the resin bed of the device can be regenerated off-line using an external source of acid to convert the entire resin bed back to the hydronium form. The constant water flow facilitates the potassium/hydronium exchange among the ion exchange sites to increase the effective suppression capacity of the device. In the capillary ion chromatography system shown in FIG. 1, the aqueous effluent from the conductivity detector can be recycled and routed through the resin bed of the capillary suppressor. Alternatively, a separate stream of deionized water may be directed through the resin bed of the suppressor to serve the same function.

As illustrated in FIG. 2, capillary tubing 32 is coiled to flow in a serpentine path. Depending on the desired length of suppressor capillary tubing to accomplish suppression, the tubing may be in a straight line or coiled or in any desired configuration. Typically, it would not be in the illustrated form with right angle turns because of the resistance to flow.

Figure 3:
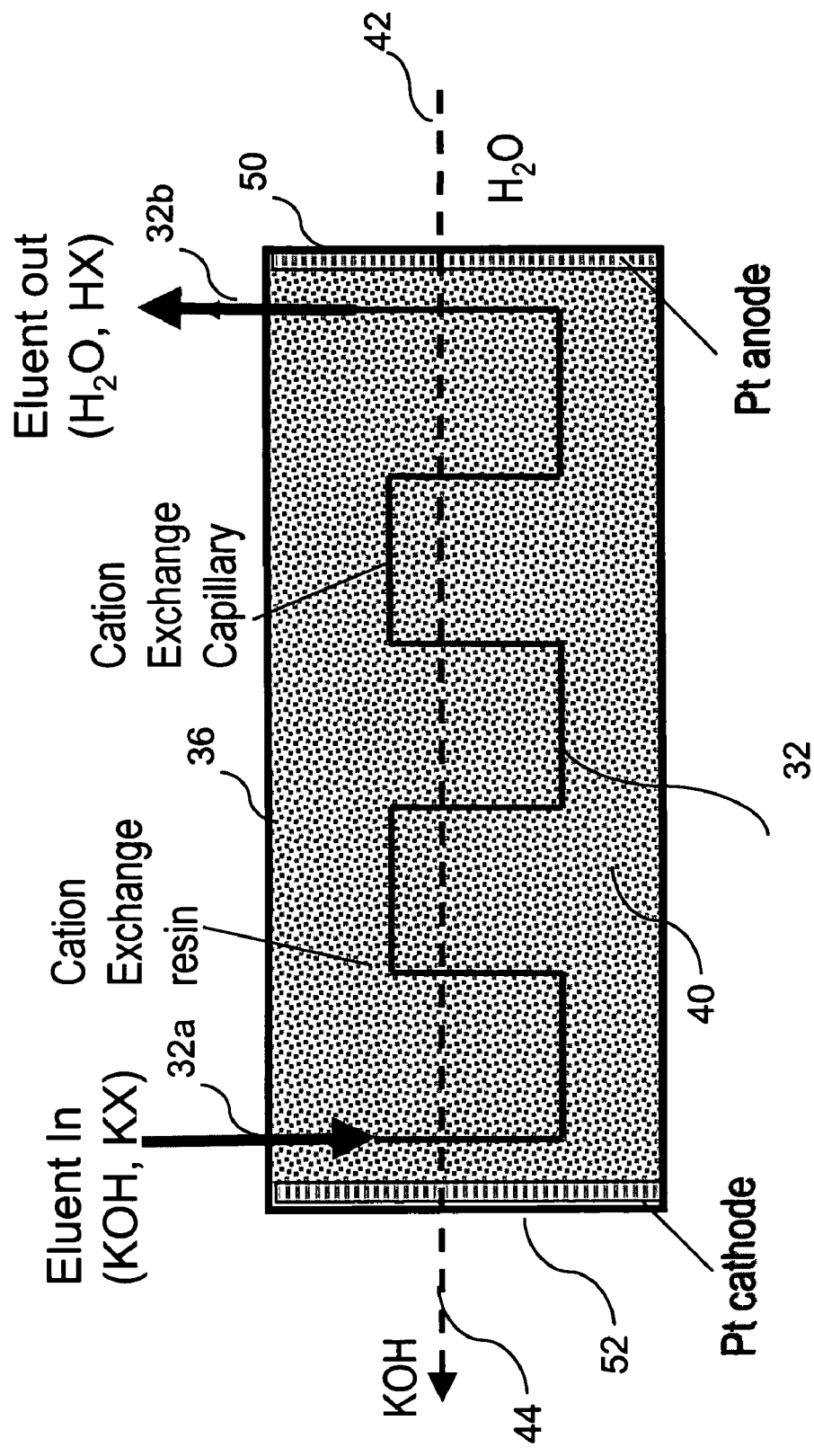

FIG. 3 illustrates an embodiment of an electrolytic capillary suppressor capable of continuous operation for anion analysis. Like parts for FIGS. 2 and 3 are illustrated with like numbers. In this embodiment, as in the embodiment of FIG. 2, the capillary anion suppressor includes a capillary tubing 32 with cation exchange sites in the inlet section embedded tightly inside a bed of cation exchange resin 40 housed in plastic column housing 32 with flow-through ports. The inlet of the resin bed is fitted with a flow-through anode 50, e.g., perforated Pt anode, and the outlet of the resin bed is fitted with a flow-through cathode 52, e.g., a perforated Pt cathode. Both electrodes are preferably in direct contact with packing 40 of the foregoing type. The cation exchange capillary tubing may be made of the foregoing materials in the foregoing dimensions. In the operation of this type of electrolytic capillary suppressor, the resin bed is continuously regenerated by hydronium ions generated through the electrolysis of water at the device anode. The principles and details of one form of continuous electrolytic suppression are illustrated in U.S. Pat. No. 6,468,804. As in FIG. 1, water in the suppressed eluent recycled from the conductivity detector is used in the electrolytic reactions. Also, as set forth above, a separate stream of deionized water may be directed through the resin bed in place of or supplemental to the recycle stream.

Figure 4:
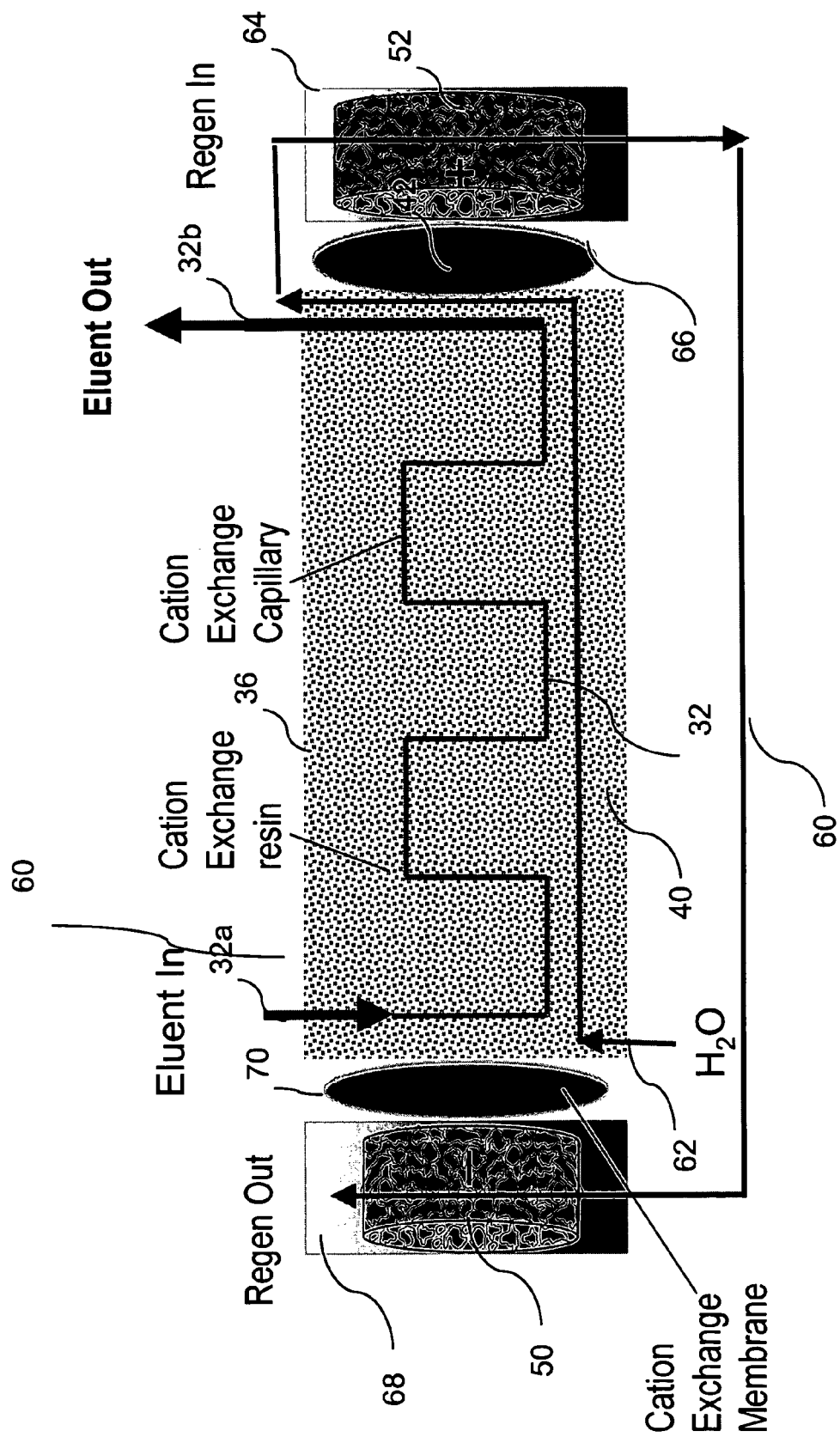

FIG. 4 illustrates another embodiment of the electrolytic capillary suppressor for anion analysis. In this embodiment, suppressor 60 includes three chambers in which the central chamber comprises ion exchange packing 40 in which capillary tubing 32 is embedded as illustrated above. Like parts designated with like numbers for FIGS. 1-3 for this part of the system. As with the device of FIG. 1, the sample-containing eluent from the chromatographic column flows into inlet 32a of the capillary tubing, and the liquid that exits capillary tubing 32b flows to the detector. The water source 62 may be recycled from a detector and/or some other source of aqueous liquid. The principal difference between the embodiments of FIGS. 3 and 4 is the presence of one or two electrode chambers out of contact with the flow through packing 40. In this instance, the solution exiting packing 40 flows into electrode chamber 64 in which anode 52 is disposed. As illustrated, optional permselective barrier 66 separates packing 40 from electrode chamber 62. The solution exiting electrode chamber 64 may be recycled in conduit 66 through electrode chamber 68 for cathode 60 which may also be separated by optional barrier 70 from packing 40. The use of separate electrode chambers with or without barriers 68 and 70 for suppressing a packed resin bed is illustrated in the embodiment of FIG. 2 of U.S. Pat. No. 6,027,643. A principal difference between these embodiments is the flow of the sample containing eluent through the resin bed is in contact with it in the '643 patent rather than through a capillary tubing within a resin bed as in the present invention. The general principles of electrolytic operation are the same for the embodiments of FIGS. 3 and 4 with the exception of the isolation of the electrodes from a flow-through the resin bed. It is preferable for the aqueous stream to be routed through the packing 40 before being sent to the anode and cathode chamber for use in the electrolytic reaction. Flow of water through packing 40 serves to remove heat generated in the operation of the electrolytic capillary suppressor.

In the above embodiments of electrolytic capillary ion suppression, suppressors can be operated continuously or intermittently. For intermittent operation, once effective suppression capacity is consumed, the resin bed can be generated electrolytically to remove eluent cations (e.g., sodium or potassium ions) to convert the packing back to the hydronium form for the next cycle. The frequency of such intermittent operation would depend on the device dimensions and the eluent influx.

To permit continuous operation without the need for off-line regeneration of packing 40, a total ion exchange capacity of the packing may be selected to correspond to the amount of capacity necessary for a particular eluent stream. For example, for electrolytic operation as in FIG. 4, the total ion exchange capacity of the packing is least 10 times to as high as 10,000 to 100,000 times or more higher than the ion exchange capacity of the capillary tubing.

By appropriate reversal of the polarity of the packing electrodes and membranes, the capillary suppressors of the prior art can be used for suppressing acid eluents for cation analysis.

Figure 5:
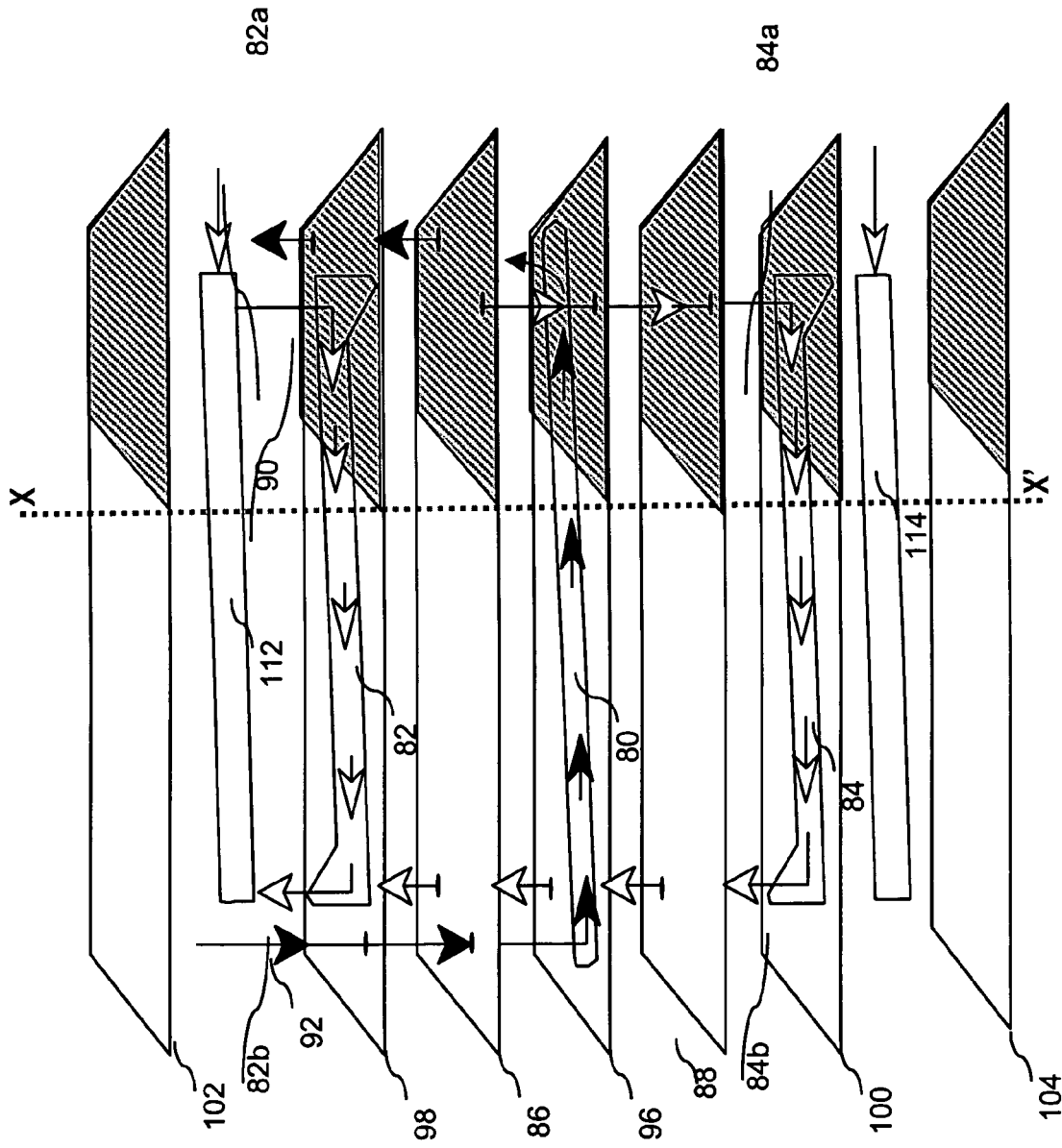

An important difference between the electrolytic suppressor shown in FIG. 4 herein and the electrolytic suppressor shown in FIG. 5 of the '733 Publication is the construction of the chromatographic effluent channel of the electrolytic suppressor of this type. In the latter suppressor, the suppressor chromatographic effluent channel is defined by the cation exchange capillary tubing made of a continuous piece of cation exchange membrane. A portion of this capillary tubing serves as the liquid inlet of the chromatographic effluent channel of the suppressor. Another portion of this piece of cation exchange capillary tubing serves as the liquid outlet of the chromatographic effluent channel of the suppressor. This outlet section of the cation exchange capillary tubing is located outside of the electromigration pathway of regenerant ions. Therefore, this outlet section of the cation exchange capillary tubing may not be regenerated rapidly upon application of electric field in the event that the chromatographic effluent channel becomes exhausted. This behavior leads to the slow recovery of the electrolytic suppressor and may hamper its performance in an ion chromatography system.

In the foregoing capillary tube embodiment of the present invention, the suppressor chromatographic effluent channel is defined by one continuous section of capillary tubing inside the housing that consists of two sections and so is termed "segmented" membrane herein. The first or inlet section of the membrane wall of the capillary is functionalized into a cation exchanger and is embedded tightly inside the bed of cation exchange resin. A portion of the inlet section of the capillary tubing serves as the liquid inlet of the chromatographic effluent channel of the suppressor and the remaining portion of the inlet section of the capillary serves as the suppression zone of the electrolytic suppressor. The second section of the capillary is substantially non-retentive, and only serves as the liquid conduit for the outlet of suppressor chromatographic effluent channel. In this embodiment of electrolytic suppressor, there is no detrimental effect if a portion of the substantially non-retentive section of capillary tubing is located outside of the electromigration passageway of regenerant ions since the outlet section of the capillary is not an ion exchanger and its function is only that of liquid conduit.

The electrolytic suppressor of the present invention with a substantially non-retentive outlet can be regenerated rapidly upon application of electric field in the event that the chromatographic effluent channels become exhausted. This is because the use of such outlet facilitates the suppressor construction or assembly such that the ion exchange portion of chromatographic effluent channel is located within the electromigration passageway of regenerate ions. This ensures that the chromatographic effluent channel can be regenerated in a rapid and efficient manner. The rapid recovery of the electrolytic suppressor improves its performance in ion chromatography.

In the capillary embodiment of FIGS. 2 and 3, the liquid conduit segment 32 is disposed in housing 36. The conduit segment includes a membrane along its length. As illustrated, the membrane is the tubular conduit. The membrane has an inlet section adjacent to the inlet of the conduit segment and a connected outlet section adjacent to the outlet of the conduit section. The inlet section is a charged ion exchange membrane, such as a Nafion®, with ion exchange sites capable of transmitting ions of one charge, positive or negative. The outlet section is substantially free of such ion exchange sites.

The foregoing advantages of these segmented conduits can be achieved with a varied portion of the outlet membrane segment in the non-functionalized form. For example, a non-functionalized outlet section ranging from about 1%, 2%, 5%, 10%, 20%, 30%, 40%, 50% or more of the total length of the membrane in the housing may be suitable depending the construction of the electrolytic suppressor.

It is preferable to exclude any substantial amount of functional packing from the outlet segment. Thus, it is preferable to use no packing or neutral packing in the interior of the non-functionalized outlet membrane segment. Ion exchange packing such as screens or ion exchange particles can be used in the interior of the inlet segment. As defined herein, the inlet segment is the portion of the conduit within the housing which is functionalized and upstream of the neutral or non-functionalized outlet segment in the housing.

Fittings for conduit 32 at inlet 32a and outlet 32b are not illustrated but may be of the conventional type. In another embodiment, not shown, the unfunctionalized outlet section of the capillary tubing may extend a significant distance outside the suppressor housing.

A portion of this extended section of the capillary may be used as the detection window for detection of target analytes using detection techniques such as contactless conductivity, UV-Vis, fluorescence and other compatible detection techniques. The end of the extended section of the capillary may also serve directly as the sample introduction inlet for other detection techniques such as mass spectrometry and inductively-couple plasma spectrometry. This function of the extended section of the capillary (i.e., the chromatographic effluent channel) eliminates the use of common couplers and other liquid connection tubing for connecting the suppressor to the detection device and thus can significantly minimize analyte peak band broadening and improve chromatographic efficiency of the ion chromatographic system.

By using appropriate anion exchange materials, the embodiments of capillary suppressors described above can also be implemented in forms that are suitable for suppressing acid eluents for determination of cationic analytes.

Figure 6:
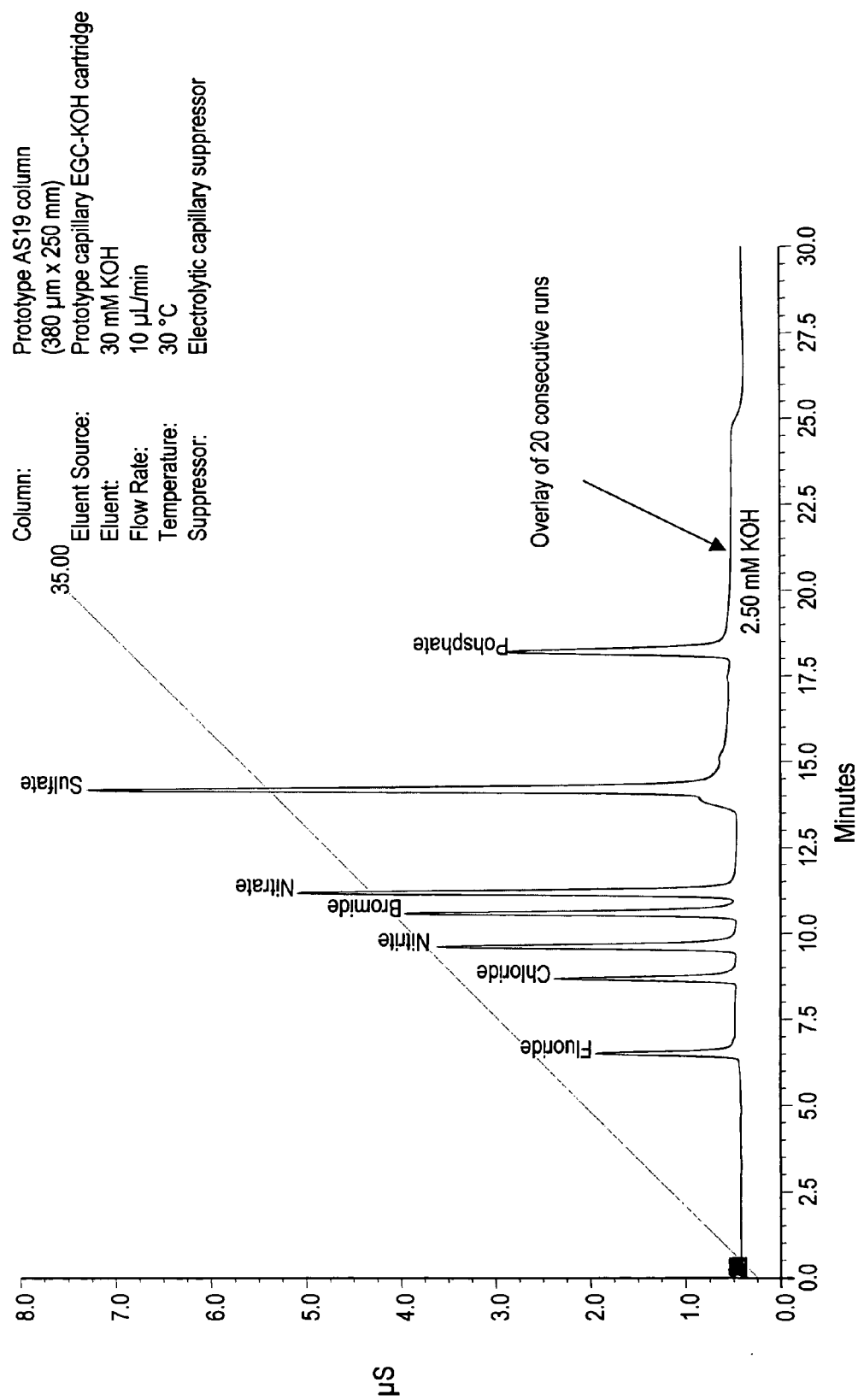
FIGS. 6-10 are charts of different experimental results illustrating the methods and apparatus of the present invention.
Figure 7:
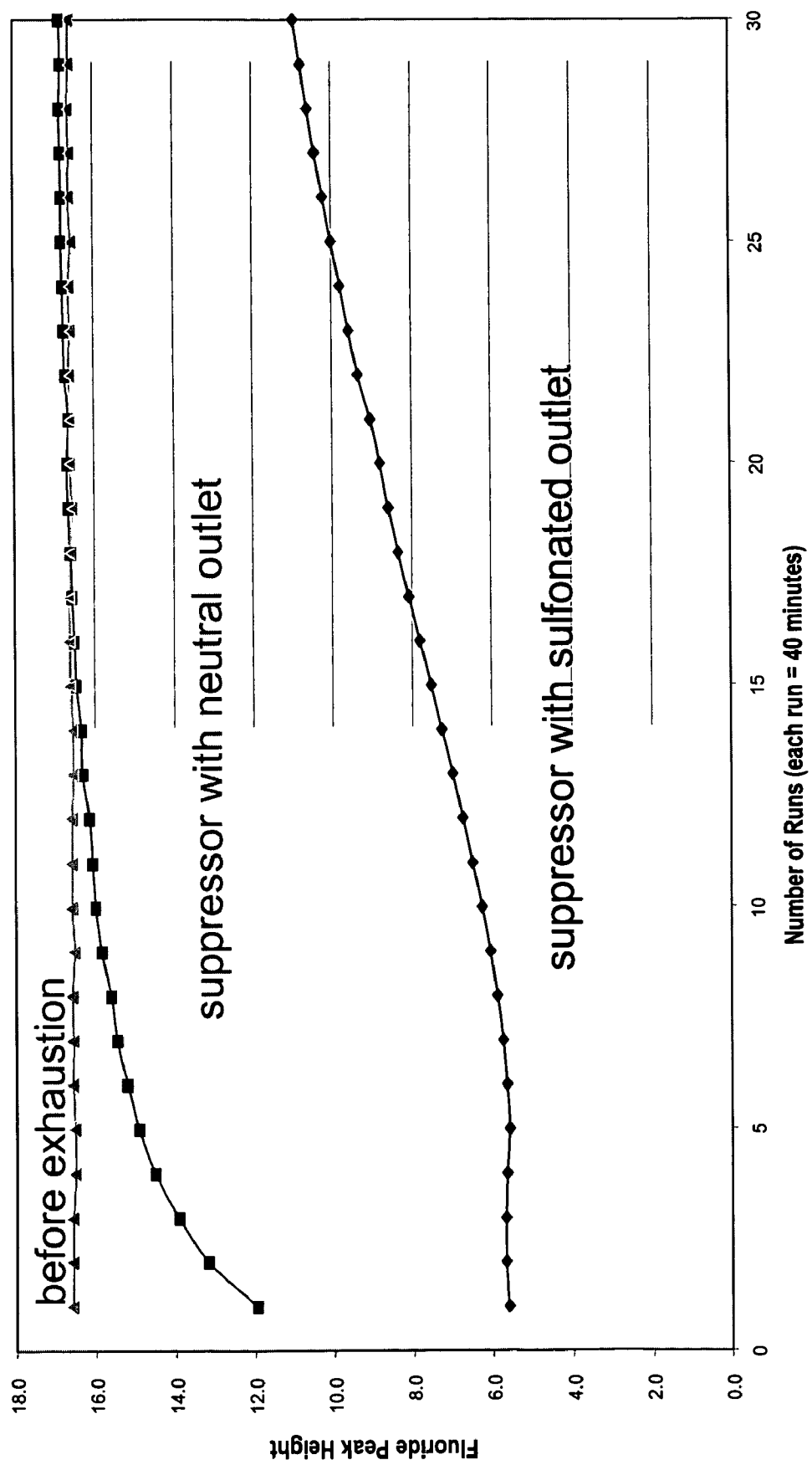
Figure 8:
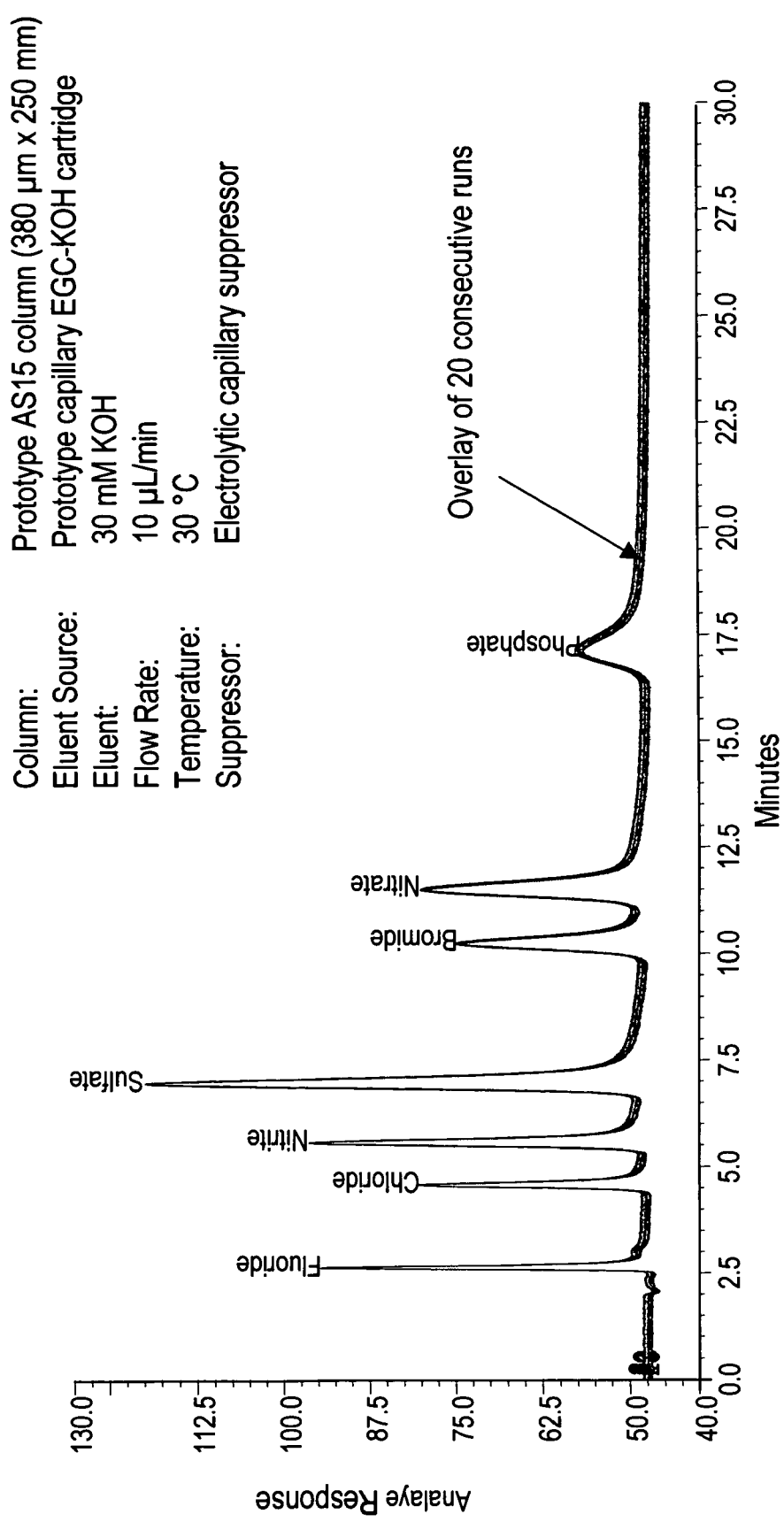

Other embodiments using a segmented membrane suppressor with a functionalized inlet section and unfunctionalized outlet section may be employed. For example, the different embodiments of membrane suppressors is disclosed in U.S. Pat. No. 6,328,885 may be employed including a flat membrane suppressor with three channels (of the sandwich type) as illustrated in FIGS. 1-4 of that patent, a two-channel device as illustrated in FIGS. 5 and 6, and a concentric tubular membrane suppressor as illustrated in FIGS. 7 and 8. In that regard, as disclosed in the '885 patent, the present invention is applicable to the electrolytic forms of all of these embodiments in which an electric field is applied transfers the flowing liquids as well as to a non-electrolytic system in which no electric field is applied. The description in the '885 patent of membrane suppressors is incorporated herein by reference.

As with the capillary tubing in the embodiment described above, the principal difference between this type of construction of the prior art and the present invention is the use of a segmented membrane bounding at least one wall of the conduit in which the inlet section of the membrane is functionalized while the outlet section is substantially free of ion exchange sites.

A sandwich suppressor useful for the present invention is illustrated in FIGS. 1-4 of the '885 patent. FIG. 5 herein is a schematic representation of a sandwich membrane suppressor of the type described in more detail in FIGS. 1-4 of the '885 patent. However, a segmented membrane is disclosed as illustrated by the line X-X'. The inlet section of the conduit for the chromatography effluent is shown to the right of the line X-X' and in the outlet section (substantially free of ion exchange sites) is shown to the right. Referring specifically to FIG. 5, the membrane suppressor includes a chromatography effluent flow channel 80 flanked by regenerant flow channels 82 and 84. As illustrated in the '885 patent, the liquid flowthrough regenerant flow channels 82 and 84 preferably is supplied by the effluent from the detector downstream from the membrane suppressor. Chromatography flow channel 80 is defined by substantially parallel membranes 86 and 88. Eluent, containing the ionic species which have been previously chromatographically separated, flows into inlet 92 to flow channel 80 and out outlet 90. Regenerant liquid flows into inlet 82*a*, flow channel 82 and out outlet 82*b* for that flow channel. In like manner, regenerant liquid flows through inlet 84*a* and out outlet 84*b* of flow channel 84. Gaskets are mounted to seal the channels between membranes 86 and 88 to define flow channels 82 and 84. External support block 102 and 104 formed of a rigid non-conductive material support and form the structural portion of the housing for the electrolytic membrane suppressor. These blocks are of the type illustrated as blocks 46 and 48 in the '885 patent.

As illustrated, ion exchange packings, preferably in the form of screens 96, 98 and 100, respectively, are used. If desired, some other form of packing such as ion exchange resin particles may be employed. In this embodiment, the segmented conduit of the present invention is defined by membranes 86 and 88 defining chromatography effluent flow channel 80. Electrode 112 is mounted adjacent to block 102 on the external side of regenerant flow channel 82 and electrode 114 is mounted adjacent to support block 104 on the external side of regenerant flow channel 84.

The membrane sheets and gasket define the outer perimeter of the chromatography effluent flow channel 80. Openings are provided for effluent inlet and outlet to the flow channel 80 as described above. To simplify connection with the external flow lines, it is preferable to form the chromatography effluent flow channel 80 slightly longer than the flanking regenerant flow channels 82 and 84. To minimize dead space, it is preferable to form both ends of effluent flow channel 80 in a V shape. The spaced electrodes are illustrated in the form of flat plate electrodes to the exterior side of the gaskets extending substantially along the length and width of the chambers in the gaskets. An electrical supply, not shown, supplies electrical potential between the device and cathode electrodes. The electrodes include openings to permit the inlet and outlet flow of detector effluent solution to the flow channels. The device of the foregoing type is relatively suitable for use in a conventional ion chromatography system with a typical operating flow rate from 0.050 to 10.0 mL/min.

The sandwich suppressor construction and operation is the same as the electrolytic sandwich suppressor set forth in the '885 patent incorporated herein by reference with the exception of the non-functionalized outlet section which is similar in effect to the capillary system described above. That is, the inlet section of the conduit for chromatography effluent flow channel 80, defined by segmented membranes 86 and 88, is functionalized, that is, includes ion exchange sites as illustrated in the '885 patent of the membranes, while the outlet section is not functionalized, (i.e., is substantially free of ion exchange sites). The same dividing line between the functionalized membrane inlet section and non-functionalized membrane outlet section of the conduit may be used.

Flow-through internal ion exchange packing may be disposed in the conduit, i.e., in the chromatography effluent flow channel 80. Preferably, the packing is in the form of a screen. The packing in forms of appropriate functionalized ion exchange resins and non-functionalized particles can also be used. The packing preferably is segmented so that inlet section adjacent to the inlet section of the membrane is functionalized while the outlet section of the packing adjacent to the outlet section of the membrane does not have ion exchange sites. Thus, the portion of the membrane suppressor channel in contact with the flowing chromatography effluent of conduit 80 is non-functionalized to the outlet side of the line X-X'.

In this way, the outlet section does not have any ion exchange properties and only serves as the liquid conduit for the outlet of flow channel 80. In this embodiment, there is no detrimental effect if a portion of the non-functionalized outlet section is outside the electromigration passageway of regenerant ion since the outlet section of channel 80 is not an ion exchanger and its function is only that of a liquid conduit. Therefore, the electrolytic suppression can be regenerated rapidly upon application of an electric field in the event that the chromatography effluent flow channel 80 becomes exhausted. The rapid recovery of electrolytic suppressor improves its performance in ion chromatography.

As in the '885 patent, by using appropriate anion exchange materials, the embodiments of suppressors described above can also be implemented in forms that are suitable for suppressing acid eluents for determination of cationic analytes Various chemical and physical approaches may be used to prepare the chromatographic effluent channels in the suppressors of the present invention as long as the suppressor effluent channel consists of an ion exchange section and a non-functionalized section. For example, functionalized polymeric-based ion exchange tubing or membrane with continuous non-functionalized section may be prepared by selective functionalization of a section of non-functionalized polymeric substrate through processes such as radiation grafting and functionalization. It is also possible to selectively mask ion exchange sites on a defined section of a continuous piece of ion exchange tubing or membrane using appropriate ionic species such as ionic surfactants that are tightly bound to the ion exchange sites. The processes involving selective chemical decomposition of ion exchange sites through chemical reactions such as oxidation on a defined section of a continuous piece of ion exchange tubing or membrane may also be used. It is also possible to form a segment of chromatographic effluent channel using appropriate functionalized ion exchange resins and another segment using non-functionalized particles.

It should be understood that other forms of the membrane suppressor may be used such as those illustrated in the '885 patent. Such forms include the use of a non-electrolytic suppressor using a regenerant solutions, use of two channel devices as illustrated in FIGS. 5 and 6 of that patent and the use of concentric tube devices as illustrated in FIGS. 7 and 8 of that patent.

In order to further illustrate the present invention, the following non-limiting examples are provided.

EXAMPLES

Example 1

Preparation of Functionalized Polymeric-Based Ion Exchange Tubing or Membrane or Screen with Continuous Non-Functionalized Section The polymeric-based cation exchange capillary tubing with continuous non-functionalized section is formed as follows. The base polymeric capillary tubing is made of a PTFE (Teflon) type supplied by Zeus Inc. (Orangeburg, S.C.). The length of the capillary tubing is typically 20 to 50 cm and its internal diameter is typically 0.001 inch to 0.010 inch with a typical wall thickness of 0.001 to 0.010 inch. A defined length of such tubing (e.g., 10 to 90% of the entire starting length of the tubing) is immersed in a solution of 30% styrene w/w in methylene chloride solvent. Grafting occurs by irradiation with gamma rays at a dose of 10,000 rads/hour for about 48-120 hours at 80-90° F. under nitrogen atmosphere. The grafted section of the PTFE tubing is then soaked in 10% w/w chlorosulfonic acid in methylene chloride for 4 hours at about 40° C. The grafted section of the PTFE tubing is then immersed in 1M KOH at 55° C. for 30 minutes.

The substrates for the ion exchange membranes are film type made of PTFE (Teflon). The substrate polymer is solvent and acid or base resistant. To prepare polymeric-based cation exchange membrane with continuous non-functionalized section, a defined section of a PTFE film is immersed in a solution of 30% styrene w/w in methylene chloride solvent. Grafting occurs by irradiation with gamma rays at a dose of 10,000 rads/hour for about 48-120 hours at 80-90° F. under nitrogen atmosphere. The grafted section of the PTFE film is then soaked in 10% w/w chlorosulfonic acid in methylene chloride for 4 hours at about 40° C. The grafted section of the PTFE tubing is then immersed in 1M KOH at 55° C. for 30 minutes.

It should be pointed out that polymeric tubing or film made of other polymeric materials such as polypropylene, polyethylene, and other fluoropolymers may be used in the preparation of functionalized polymeric-based ion exchange tubing or membrane with continuous non-functionalized section.

Example 2

Preparation of Functionalized Polymeric-Based Ion Exchange Tubing or Membrane or Screen with Continuous Non-Functionalized Section Through Selective Decomposition of Ion Exchange Sites This example describes the method to prepare the polymeric-based cation exchange capillary tubing with continuous non-functionalized section through selective decomposition of ion exchange sites on a defined section of a continuous piece of ion exchange material such as tubing, membrane or screen. The preparation of cation exchange membrane with continuous non-functionalized section is given as an example.

A piece of fully sulfonated ion exchange membrane was prepared using a PTFE film as the starting material as described in Example 1. A defined section of this piece of sulfonated membrane was then immersed in a reaction vessel containing a solution of 6% sodium hypochlorite while the remaining section of the membrane was not in contact with the sodium hypochlorite solution. The reaction vessel containing with the immersed section of the membrane was heated to 80° C. for 2 to 48 hours to remove grafted ion exchange sites on the immersed section of the membrane. After the reaction, the treated section of membrane was converted back to the non-functionalized PTFE substrate form and thus a piece of sulfonated ion exchange membrane with continuous non-functionalized section was obtained.

The same process was also used to prepare radiated-grafted anion exchange membrane with continuous non-functionalized section.

Example 3

Separation of Common Anions Using Capillary Ion Chromatography System Employing a Capillary Electrolytic Suppressor with Non-Functionalized Outlet Section This example demonstrates the use of electrolytic capillary anion suppressors of the type depicted in FIG. 4 in the capillary IC separation of common anions. The capillary IC system used in the experiment was constructed according to the scheme shown in FIG. 1. A modified Dionex P680 pump (Dionex Corporation, Sunnyvale, Calif.) was used to deliver deionized water at 12 µL/min. To generate a KOH eluent, deionized water was first passed through Dionex ATC-HC and CTC-1 columns to remove ionic contaminants and then routed into a KOH eluent generator that was prepared by modifying a Dionex EGC-KOH cartridge (P/N 058900). A Keithley Model 220 Programmable Current Source (Keithely Instruments, Inc., Cleveland, Ohio) was used to supply the DC current to the anode and cathode of the KOH eluent generator. The outlet of the KOH eluent generator was connected to a high-pressure degas unit to remove hydrogen gas generated during the electrolytic eluent generation process. A Rheodyne six-port PEEK high-pressure injection valve (Cotati, Calif.) was used for injection of samples. The capillary anion separation column was prepared by packing a proprietary Dionex surface-functionalized anion exchange resin in a 1/16-inch OD PEEK tubing of 250 mm in length and 380 μm in internal diameter. A Dionex ED50A conductivity detector equipped with a modified flow-through conductivity cell was used. A Dionex Chromeleon 6.6 chromatography data system was used for instrument control, data collection, and processing.

In this example, electrolytic capillary suppressors were prepared according the basic scheme illustrated in FIG. 4. The capillary anion suppressors consisted of three PEEK chambers. The eluent chamber contained a cation exchange capillary tubing embedded tightly inside a bed of cation exchange resin (8 mm ID×20 mm in length). The chromatographic eluent channel of the suppressor was made of a piece of PTFE capillary tubing of 25 cm in length. The PTFE capillary tubing had an internal diameter of 0.004 inch and an outer diameter of 0.010 inch. A 15-cm section of the PTFE capillary tubing was functionalized into a sulfonated cation exchanger and another 10-cm section of PTFE capillary tubing was not functionalized using the procedure described in Example 1. Provisions were made to provide separate fluid connections to the PTFE capillary tubing in the resin bed. The sulfonated section of the PTFE capillary tubing was used the inlet of the chromatographic effluent inlet. The non-functionalized end of the PTFE capillary tubing was used as the chromatographic effluent inlet.

The eluent chamber was physically separated from the cathodic regenerant chamber and anodic regenerant chamber using proprietary grafted and sulfonated PTFE cation exchange ion exchange membranes (Dionex Corporation). The cathode chamber contained a perforated Pt cathode and the anode chamber contained a perforated Pt anode. Both electrode chambers had two liquid connecting ports (inlet and outlet). In this example, the suppressed eluent from the conductivity cell was routed to waste. A second stream of deionized water was first pumped through the resin bed in the eluent chamber, then to the anodic regenerant chamber and the cathodic regenerant chamber at flow rates ranging from 0.1 to 0.25 mL/min. The Dionex ED50A module was used to supply a DC current of 20 mA to the electrolytic capillary suppressors. A Dionex EG40 eluent generator control module was used to supply DC currents to the KOH eluent generation cartridge for generation of KOH eluents used in the ion chromatographic separations of anions.

FIG. 6 shows an overlay of 20 consecutive separations of the separation of fluoride, chloride, bromide, nitrite, nitrate, sulfate, and phosphate on a capillary column packed with a proprietary surface-functionalized anion exchanger (Dionex Corporation obtained using the system. The separation was performed using 30 mM KOH at a flow rate of 10 μL/min. The analyte retention time percent relative standard deviation (RDS) ranges from 0.03% for sulfate to 0.07% for fluoride. The analyte peak area response percent RSD ranges from 0.46% for bromide to 1.1% for fluoride The results show that the system of the present invention is capable of providing highly reproducible separation of the target anions In one experiment, the chromatographic effluent channel of the suppressor was changed completely into an exhausted state (i.e., in the K+ form) by passing the KOH solution through the chromatographic effluent channel of the suppressor. The suppressor was supplied with 30 mA of current so that it could be electrolytically regenerated. At the same time, the system was used to perform the separation of fluoride, chloride, nitrate, sulfate, and phosphate. The peak area responses of target analytes were closely monitored. It was observed that the peak area response would increase over time as the suppressor was regenerated electrolytically. As a comparison, the same experiment was repeated using the same capillary suppressor by reversing the flow direction of the chromatographic channel of the suppressor. In the reversed flow direction, the outlet section of the chromatographic effluent channel contains ion exchange sites. FIG. 7 shows the recovery of recovery behaviors of these two suppressors in which the peak area response of fluoride was plotted against the number of injections initiated immediately after the electrolytic regeneration of the exhausted suppressors was started.

The results show that the peak area response obtained using the capillary suppressor with the non-functionalized outlet section increased much faster than the capillary suppressor with the functionalized outlet section. Therefore, the results demonstrate clearly that the electrolytic suppressor of the present invention can be regenerated more rapidly upon application of electric field in the event that the chromatographic effluent channels become exhausted. The rapid recovery of electrolytic suppressor improves its performance in ion chromatography.

Example 4

Separation of Common Anions Using Capillary Ion Chromatography System Employing a Capillary Electrolytic Suppressor with Non-Functionalized Outlet Section and Contact Less Conductivity Detection This example demonstrates the use of electrolytic capillary anion suppressors of the type depicted in FIG. 4 in the capillary IC separation of common anions. The capillary ion chromatography system used in example had the same system components as the system described in Example 3. The capillary electrolytic suppressor was constructed in a manner similar to the one described in Example 2. However, the length of the non-functionalized section of the PTFE capillary tubing serving as the chromatographic effluent channel was increased to 20 cm. his section of the non-functionalized capillary tubing was extended outside of the housing of the electrolytic suppressor. A portion of the extended section of the capillary was used as detection window for detection of target analytes using a prototype high frequency capacitively coupled contactless conductivity detector developed by Dionex Corporation.

FIG. 8 shows the separation of seven common anions (fluoride, chloride, bromide, nitrite, nitrate, sulfate, and phosphate) obtained using the system described above. The separation was performed using a KOH eluent (30 mM KOH) at 10 μL/min. The results show highly reproducible separation of the target anions. The analyte retention time percent relative standard deviation (RDS) ranged from 0.08% for fluoride to 0.20% for phosphate and the analyted peak area percent RSD ranged from 1.1% for fluoride to 3.0% for sulfate over 20 consecutive injections. The above results demonstrate that the capillary IC system described in this invention can be used to provide reliable determination of target anionic analytes.

Example 5

Separation of Common Anions using an Ion Chromatography System Employing a Sandwich-Type Electrolytic Membrane Suppressor with Non-Functionalized Outlet Section This example illustrates the use of the ion chromatography system employing a sandwich-type electrolytic membrane suppressor with non-functionalized outlet section for determination of common anion including fluoride, chloride, bromide, nitrite, nitrate, sulfate, and phosphate. A Dionex DX500 ion chromatography system consisting of a dual-piston high pressure pump, a six-port injector, a column oven, and a conductivity detector was used. A Dionex 4-mm AS17 column was used as the separation column, a solution of 15 mN KOH was used as the eluent, and the separation was performed at 1.0 mL/min. A sandwich-type electrolytic membrane suppressor with non-functionalized outlet section was assembled according to the basic scheme illustrated in FIG. 5 and used in the experiments. An applied current of 100 mA was used in operation of the suppressor.

Figure 9:
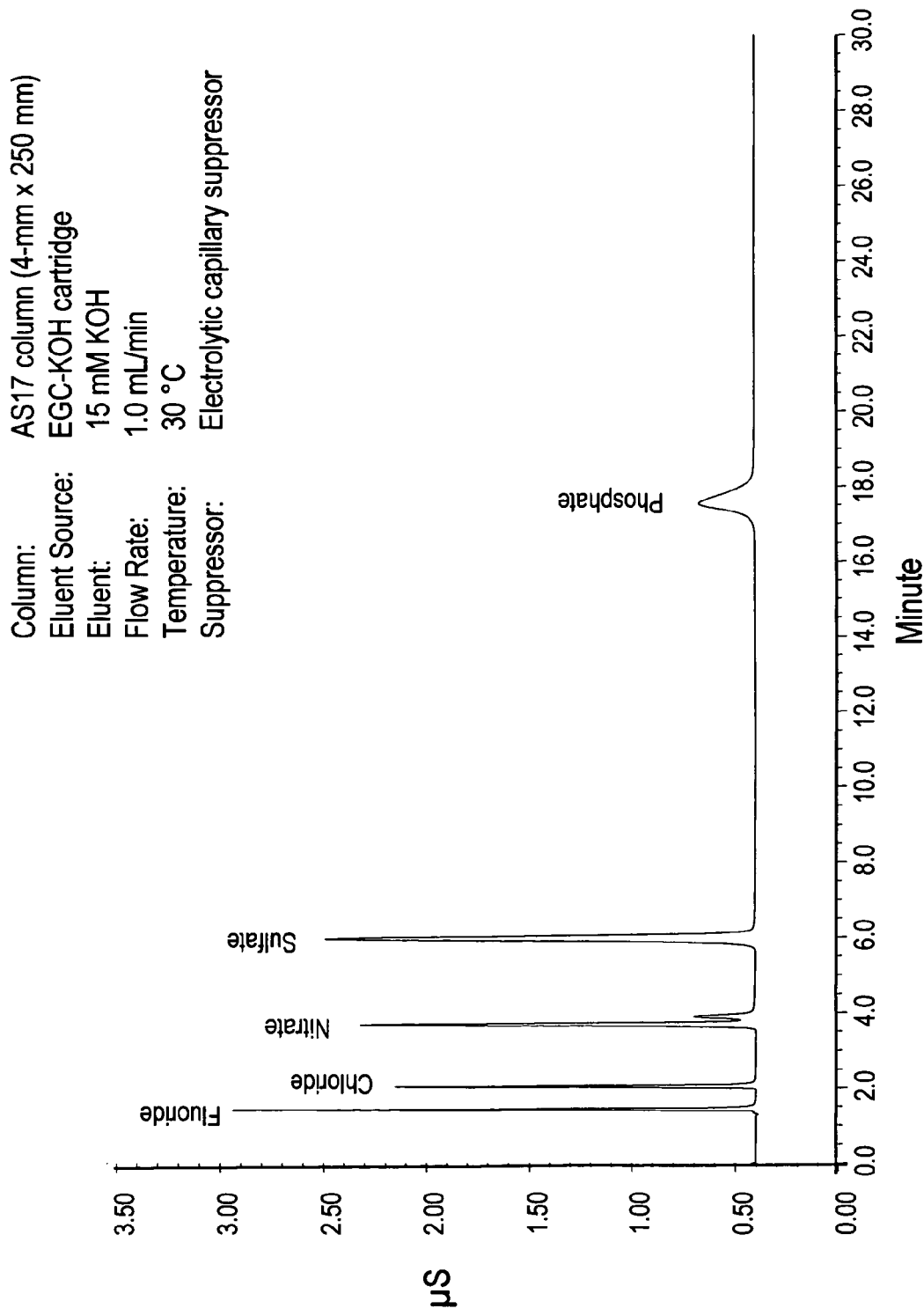
Figure 10:
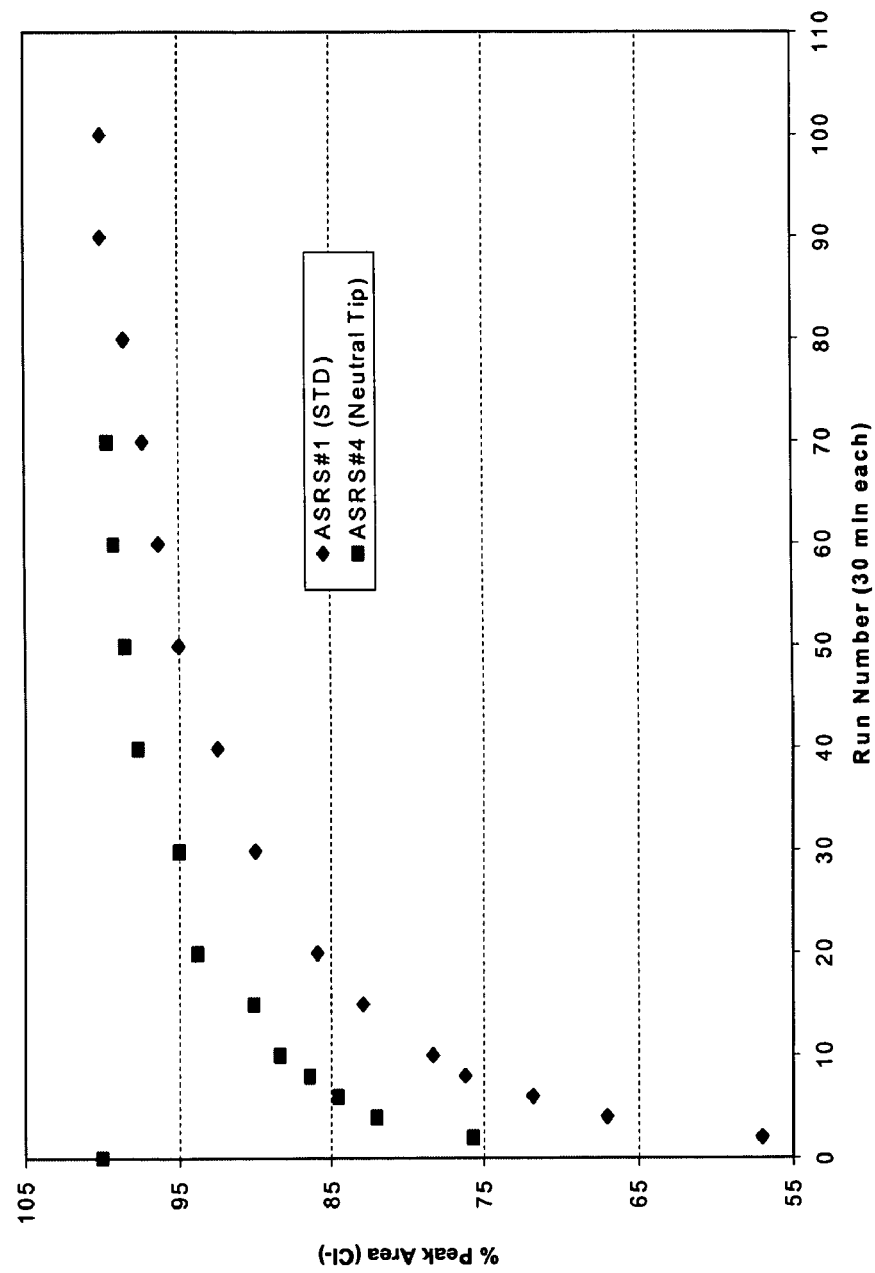

FIG. 9 shows the separation of fluoride, chloride, bromide, nitrite, nitrate, sulfate, and phosphate obtained using the system. In one experiment, the system was allowed to operate to the state that stable and reproducible peak areas for fluoride, chloride, bromide, nitrite, nitrate, sulfate, and phosphate were obtained. At this point, the DC current applied to the suppressor was turned off and the eluent of 15 mM KOH was pumped continuously into the chromatographic effluent channel of the suppressor for 240 minutes. During this period, the chromatographic effluent channel of the suppressor changed completely into an exhausted state (i.e., in the K+ form). After 240 minutes, the suppressor was applied with 100 mA of current so that it could be electrolytically regenerated. At the same time, the system was used to perform the separation of fluoride, chloride, bromide, nitrite, nitrate, sulfate, and phosphate. The peak area responses of target analytes were closely monitored. It was observed that the peak area response would increase over time as the suppressor was regenerated electrolytically. As a comparison, the same experiment was repeated using a DIONEX 4-mm ASRS suppressor (a commercially available sandwiched type suppressor that does not have the feature of non-functionalized outlet section). FIG. 10 shows the recovery behaviors of these two suppressors in which the peak area response of fluoride was plotted against the number of injections initiated immediately after the electrolytic regeneration of the exhausted suppressors had been started. The results show that the peak area response obtained using the suppressor of the present invention (data points denoted as "ASRS#4 neutral tip" in FIG. 10 increased faster than the standard ASRS suppressor (data points denoted as "ASRS #1 (STD)" in FIG. 10. Therefore, the results demonstrate clearly that the electrolytic suppressor of the present invention can be regenerated more rapidly upon application of electric field in the event that the chromatographic effluent channels become exhausted. The rapid recovery of electrolytic suppressor improves its performance in ion chromatography

What is claimed is:

1. Apparatus for ion chromatography comprising a suppressor comprising a housing and a liquid conduit segment disposed in said housing, said liquid conduit segment including a membrane, said membrane being continuous and having an inlet section adjacent the inlet of said conduit segment and an outlet section adjacent the outlet of said conduit segment, said inlet section having ion exchange sites capable of transmitting ions of one charge, positive or negative, and said outlet section being substantially non-retentive electrostatically for charged ionic species.

2. The apparatus of claim 1 in which said outlet section is substantially free of ion exchange sites.

3. The apparatus of claim 1 further comprising flow-through internal ion exchange packing disposed in said conduit segment adjacent the membrane inlet section but not adjacent the membrane outlet section.

4. The apparatus of claim 1 in which said conduit comprises tubing formed of said membrane.

5. The apparatus of claim 4 in which said tubing is capillary tubing.

6. The apparatus of claim 5 further comprising flow-through external ion exchange packing disposed in said housing, said tubing being at least partially disposed in said external ion exchange packing.

7. The apparatus of claim 6 further comprising a source of flowing aqueous liquid in fluid communication with said external ion exchange packing.

8. The apparatus of claim 6 further comprising a capillary chromatography column in contact with said capillary tubing inlet section.

9. The apparatus of claim 8 further comprising a flow-through detector in fluid communication with said capillary tubing outlet section.

10. The apparatus of claim 9 in which said electrostatically substantially non-retentive conduit outlet section extends through said flow-through detector forming a detection window thereof.

11. The apparatus of claim 6 further comprising spaced first and second electrodes on opposed sides of said ion exchange packing.

12. The apparatus of claim 1 in which said membrane comprises at least a first substantially flat membrane comprising one wall of said conduit.

13. An ion chromatography method comprising flowing an aqueous stream comprising separated ionic species of one charge, positive or negative, in an eluent through a suppressor comprising a liquid conduit segment including a membrane, said membrane being continuous and having an inlet section adjacent the inlet of said conduit segment and an outlet section adjacent the outlet of said conduit segment, said inlet section having ion exchange sites capable of transmitting ions of one charge, positive or negative, said outlet section being substantially non-retentive for said charged ionic species, to transport counter ions in said eluent of opposite charge to said separated ionic species out of said conduit segment across said membrane.

14. The method of claim 13 in which said outlet section is substantially free of ion exchange sites.

15. The method of claim 13 in which flow-through internal ion exchange packing is disposed in said conduit adjacent the membrane inlet section but not adjacent the membrane outlet section.

16. The method of claim 14 in which said conduit comprises tubing formed of said membrane.

17. The method of claim 14 in which said tubing is capillary tubing.

18. The method of claim 16 in which said tubing is at least partially disposed in flow-through external ion exchange packing disposed in a housing.

19. The method of claim 18 further comprising flowing a liquid stream though said external ion exchange packing.

20. The method of claim 13 in which said ionic species are separated in a capillary chromatography column prior to flow through said suppressor.

21. The method of claim 13 further comprising detecting said separated ionic species exiting from said suppressor.

22. The method of claim 15 further applying an electric field across said internal ion exchange packing.

* * * * *